United States Patent
Junio et al.

(10) Patent No.: US 8,221,371 B2
(45) Date of Patent: Jul. 17, 2012

(54) WRAPPER SEALING PROCESS AND ARTICLE

(75) Inventors: Joseph Junio, Edison, NJ (US); David L. Kimball, Flemington, NJ (US); Ralf Mueller, Duesseldorf (DE); Tony Ng, East Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 457 days.

(21) Appl. No.: 12/444,656

(22) PCT Filed: Oct. 12, 2007

(86) PCT No.: PCT/US2007/081194
§ 371 (c)(1),
(2), (4) Date: Apr. 7, 2009

(87) PCT Pub. No.: WO2008/046036
PCT Pub. Date: Apr. 17, 2008

(65) Prior Publication Data
US 2010/0022980 A1    Jan. 28, 2010

Related U.S. Application Data

(60) Provisional application No. 60/829,227, filed on Oct. 12, 2006.

(51) Int. Cl.
*A61F 13/15* (2006.01)
*A61F 13/20* (2006.01)
*A61L 15/00* (2006.01)
*B65B 11/00* (2006.01)
*B26D 7/27* (2006.01)

(52) U.S. Cl. ......... 604/385.02; 604/385.01; 604/385.17; 604/385.18; 604/904; 28/118; 206/438; 206/440; 53/461; 53/396

(58) Field of Classification Search ............. 604/385.02, 604/385.01, 385.17, 385.18, 904; 206/440, 206/438; 28/118; 53/396, 461
See application file for complete search history.

(56) References Cited

U.S. PATENT DOCUMENTS

| | | |
|---|---|---|
| 1,926,900 A | 9/1933 | Haas |
| 3,278,013 A | 10/1966 | Banks |
| 3,422,496 A | 1/1969 | Wolff et al. |
| 3,674,029 A | 7/1972 | Bates et al. |
| 3,811,445 A | 5/1974 | Dostal |
| 3,929,135 A | 12/1975 | Thompson |
| 3,983,875 A | 10/1976 | Truman |
| 4,170,305 A | 10/1979 | Hull, Jr. et al. |
| 4,381,326 A | 4/1983 | Kelly |

(Continued)

FOREIGN PATENT DOCUMENTS

EP     422660 A     4/1991

(Continued)

*Primary Examiner* — Jacqueline F. Stephens

(57) ABSTRACT

A process for overwrapping a catamenial device such as a tampon includes the steps of providing a substantially cylindrical overwrapper material, inserting a catamenial device into the overwrap material, and closing the open end of the overwrapper material. The overwrapper material has an open end, a closed end, and a first length. The catamenial device has a tapered insertion end, a longitudinal axis, and a length less than the first length, such that the open end of the overwrapper material extends beyond the insertion end of the inserted catamenial device. Concave clamping jaws are applied to the open end of the overwrapper material to urge it toward the longitudinal axis of the catamenial device; to conform portions of the overwrapper material to the insertion end of the catamenial device; and to fold overwrapper material between adjacent clamping jaws to form fins extending outwardly from the conformed portions.

16 Claims, 8 Drawing Sheets

U.S. PATENT DOCUMENTS

| | | |
|---|---|---|
| 5,567,376 A | 10/1996 | Turi et al. |
| 5,911,712 A | 6/1999 | Leutwyler et al. |
| 6,010,001 A | 1/2000 | Osborn, III |
| 6,131,736 A | 10/2000 | Farris et al. |
| 6,183,457 B1 | 2/2001 | Kuhn |
| 6,310,296 B1 | 10/2001 | Nishi et al. |
| 6,465,713 B1 | 10/2002 | Gell et al. |
| 6,554,814 B1 | 4/2003 | Agyapong et al. |
| 6,955,665 B2 | 10/2005 | Domeier et al. |
| 7,101,358 B2 | 9/2006 | Domeier et al. |
| 2003/0220624 A1 | 11/2003 | Domeier et al. |
| 2004/0133142 A1 | 7/2004 | Lochte et al. |
| 2004/0192130 A1 | 9/2004 | Baciu et al. |
| 2005/0256511 A1 | 11/2005 | Chase et al. |
| 2005/0283128 A1 | 12/2005 | Chase et al. |
| 2008/0118679 A1 | 5/2008 | McConnell et al. |

FOREIGN PATENT DOCUMENTS

| | | |
|---|---|---|
| EP | 597446 A | 5/1994 |
| EP | 1010622 A | 6/2000 |
| GB | 740803 A | 11/1955 |
| JP | 10072057 A | 3/1998 |
| RU | 2233648 C2 | 8/2004 |
| WO | WO 01/01909 A | 1/2001 |
| WO | WO 01/15994 A | 3/2001 |
| WO | WO 01/36272 A | 5/2001 |
| WO | WO 03/082174 A | 10/2003 |
| WO | WO 2004/080362 A1 | 9/2004 |
| WO | WO 2005/112860 A | 12/2005 |

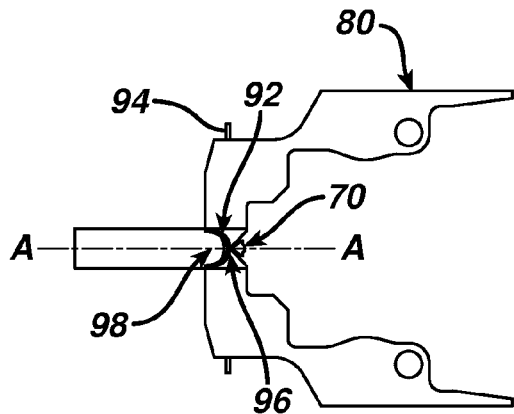 
FIG. 9A  FIG. 9B
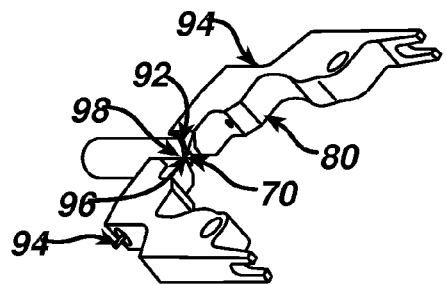
FIG. 9C
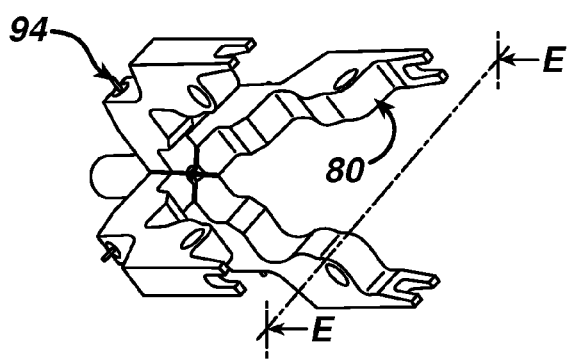 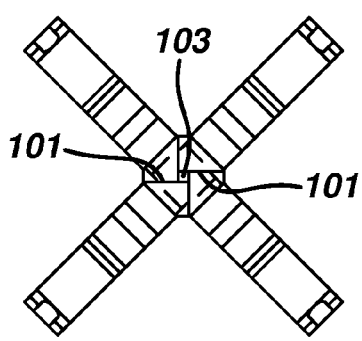
FIG. 9D  FIG. 9E

WRAPPER SEALING PROCESS AND ARTICLE

CROSS REFERENCE TO RELATED APPLICATIONS

This application is the national stage filing of international application PCT/US2007/081194 filed on Oct. 12, 2007, which claims the benefit of U.S. provisional application 60/829,227 filed on Oct. 12, 2006, both of which are hereby incorporated herewith by reference.

FIELD OF THE INVENTION

This invention is related to wrapped cylindrical bodies and in particular catamenial devices useful in absorbing bodily fluids.

BACKGROUND OF THE INVENTION

Overwrappers for cylindrical bodies and in particular overwrappers for products which can be easily opened but at the same time should be protected from dirt, dust, moisture or other contamination while wrapped such as, for example, catamenial tampons are popular ways to provide individual, portable articles. While the invention will be discussed specifically in terms of catamenial tampons, it will be understood that the problems toward which this invention is directed and their solution applies to many similar products, including, for example, foods, tobacco products and the like.

One method and apparatus for closing a packing tube is disclosed in WO 01/36272 (Buzot et al). In this publication, a packing tube is closed around an essentially cylindrical packaged product. The packing tube is projected beyond a free forward end of the product is pressed together and joined by heated clamping jaws to form a first film sheet. The formed first film sheet portion is then folded over and laid onto the outer surface of packing tube at the forward end. Sealing of the folded sheet is accomplished by application of heated dome shaped pressing head. The inner walls surrounding the recess of the heated pressing head melts the folded sheet with the film of the outer surface of the packing tube. Sufficient heat needs to be applied to melt the three layers of film together. Additionally, the heated jaws need to conform to the geometry or curvature of the insertion end of the tampon in order for the melted film to provide a tight fit of the overwrap.

New development in catamenial tampons now include those that have covers or fluid transport plates such as those disclosed in US 20050256511, US 20050283128 and WO 2005/112860. In these new types of tampons, by-pass leakage is reduced as the fluid transport plates serve to direct fluid to a fluid storage element. One example of such a tampon is one that includes as fluid transport plates a sheet of apertured film, which covers the insertion portion of the fluid storage element and is attached to the fluid storage element by a longitudinal heat seal. This differs from previous tampons in many ways, including the fact that an apertured film covers the insertion portion of the tampon, which typically has been left uncovered. WO 01/01909 discloses a domed tampon having an absorbent structure substantially enclosed by an apertured film cover that has a nonionic surfactant at least partially applied to the cover. The cover overlaps the domed-shaped introduction end but does not completely cover it. One problem encountered in the type of tampon that has a meltable material at the insertion portion of the tampon relates to providing and heat sealing an overwrap. The heat sealing of the overwrap generally occurs at the insertion end and withdrawal end. When heat is supplied to the overwrap material, the apertured film covering the insertion portion of the tampon is also subjected to the heat. The film may melt, the apertures may close and the film may become attached to the overwrap.

What is needed therefore, is a way to seal the overwrap without melting the apertured film covering the insertion portion of the tampon. In particular what is needed is a way to seal a cover or fluid transport element made of a material having a melting point equal to or less than the melting point of the overwrap. One difficulty in overcoming this problem is the geometry of the insertion end of the tampon. This invention solves this problem and provides an overwrapped catamenial device, a method for overwrapping a catamenial device and an apparatus useful for providing this overwrapped catamenial device.

SUMMARY OF THE INVENTION

The process for overwrapping a catamenial device such as a tampon includes:
  Providing a cylindrical overwrapper having a length greater than the object it will be overwrapping
  inserting a catamenial device within the overwrapper such that the overwrapper extends outward from the catamenial device at the insertion end, the cylindrical body having an domed insertion end;
  heat sealing the overwrapper at the withdrawal end of the cylindrical body
  contacting the extending overwrapper at the domed insertion end with at least three concave clamping jaws, each clamping jaw heated to a temperature minutes;
  removing the at least three clamping jaws
wherein the overwrap forms a seam over the insertion end such that the overwrap fins are capable of being folded over to conform to the insertion end of the overwrap.

In one aspect of the present invention, an overwrapped catamenial device for absorbing bodily fluids has a cylindrical body having an insertion end and withdrawal end, the insertion end having a dome shape; and a generally cylindrical overwrapper having a first open end and a second closed end. The ends of the overwrap corresponding to the insertion end and the withdrawal end respectively, and the cylindrical body is contained within the cylindrical overwrap. The first open end of cylindrical overwrap extends beyond the dome and forms at least three radial sections extending from a longitudinal axis, which when sealed together form a flat seam which has a curvilinear arc about said dome and a portion extending away from the dome. This may also include folding the seam toward the dome.

In another aspect of the invention, an apparatus includes a clamping device, and a finishing former. The clamping device has a plurality of sealing jaws, each jaw having a first end and a second end. The first end is heated to a temperature that causes the overwrap to soften, and it is adapted to receive the cylindrical article such that when the first end of the jaws contacts the cylindrical article the overwrap is molded about the cylindrical article and seals to form a plurality of fins having at least 3 radial sections. The finishing former folds the fins over onto the molded overwrap about the cylindrical article.

BRIEF DESCRIPTION OF THE DRAWING

FIG. 7 shows four views of a single jaw of the present invention:

FIG. 8 shows four views of four jaws forming the apparatus:

FIG. 9 shows five views of four jaws forming an alternative embodiment of the apparatus:

FIG. 9A shows a side elevation of two opposed jaws of the apparatus with a tampon disposed in the recess of the apparatus;

FIG. 9B shows an end elevation of the two jaws of FIG. 9A from the view of line B-B;

FIG. 9C shows a perspective view of the two jaws of FIG. 9B in the closed position;

FIG. 9D shows a perspective view of four jaws in the closed position; and

FIG. 9E shows an end elevation of the four jaws of FIG. 9D from the view of line E-E.

DETAILED DESCRIPTION OF THE PREFERRED EMBODIMENTS

Figure 1:
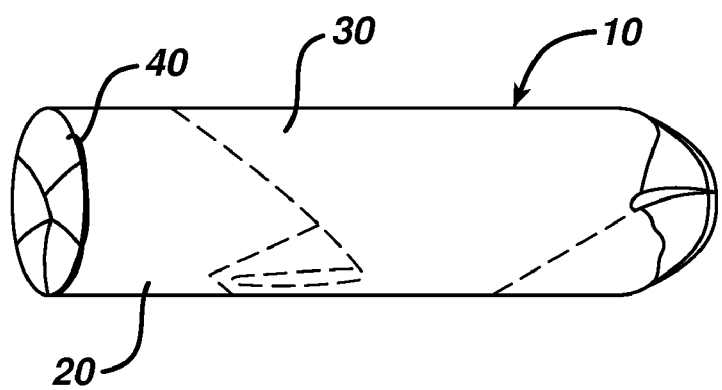
FIG. 1 shows a perspective view of an overwrapped tampon of the present invention.

Referring now to the drawings, illustrated in FIG. 1 is an example of a wrapped cylindrical body 10 of this invention. The wrapped cylindrical body 10 has an overwrap 20 and specifically a catamenial tampon 30, which is shown in greater detail in FIG. 2. The overwrap 20 is a flexible, tearable, generally moisture and vapor resistant material for the purpose of cleanliness and also to preserve its shape. For the sake of clarity, tear strip 26 is shown only in FIG. 3.

Figure 2:
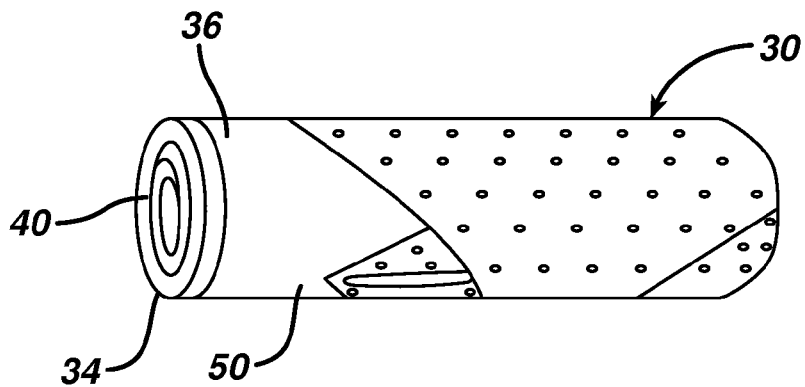
FIG. 2 shows a perspective view of a tampon having an insertion end which has a secondary cover.
Figure 3:
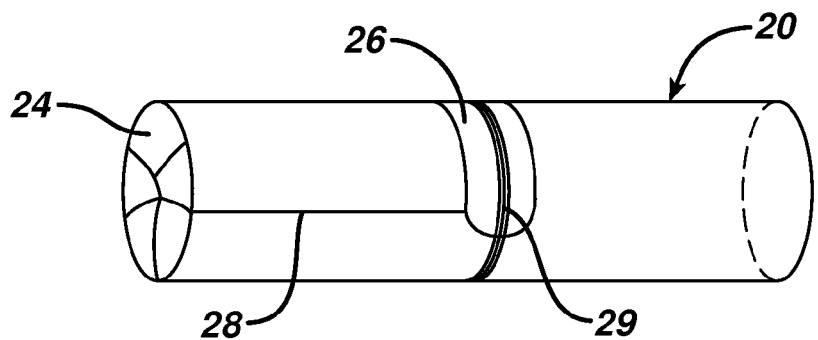
FIG. 3 shows a perspective view of a tubular overwrap before insertion of a tampon.
Figure 4:
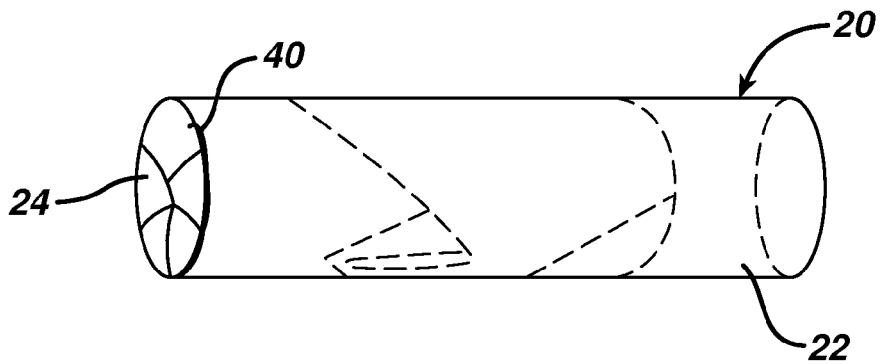
FIG. 4 shows a perspective view of a tubular overwrap sealed at the withdrawal end containing a tampon.

The tampon 30 has an insertion end 32 and a withdrawal end 34. The withdrawal end may include a removal string 40. In FIG. 2, the withdrawal string is shown in a wound configuration. During use, the user would unwind the removal string and have it extending away from the tampon. In one embodiment, the insertion end is domed. By domed it is meant that the end of the tampon is not flat and has a rounded or hemispherical shape. In another embodiment, the insertion end has a more flattened geometry. This invention can be adapted to any type of geometry that the insertion end of a tampon may have.

Figure 5:
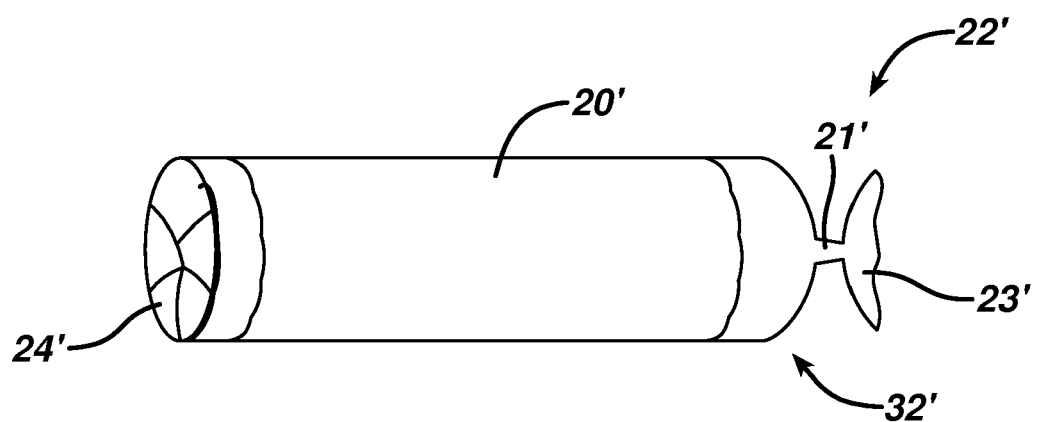
FIGS. 5 and 6 show perspective views of tampon having an overwrap sealed by a known method of the prior art.
Figure 6:
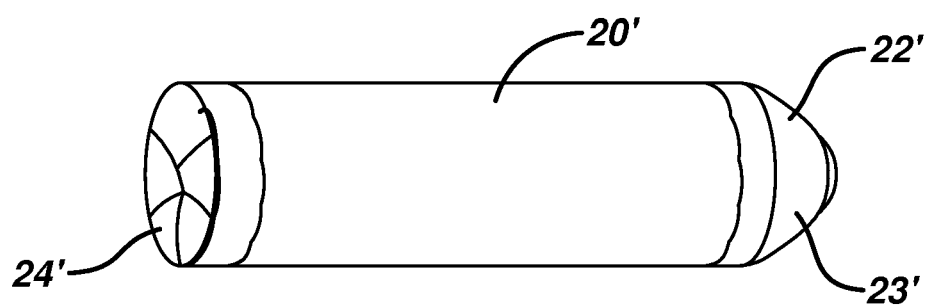
Figure 7A:
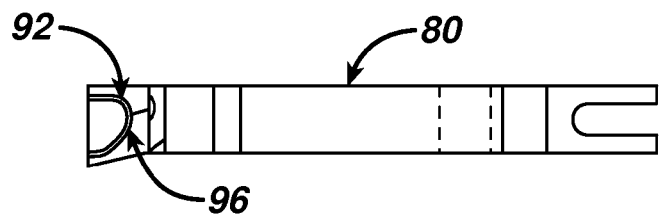
FIG. 7A shows a plan view of the inner face of the jaw from the longitudinal central axis of the apparatus.
Figure 7B:
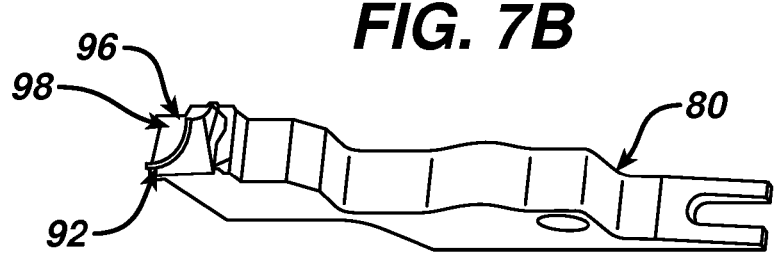
FIG. 7B shows a perspective view of the inner face of the jaw.
Figure 7C:
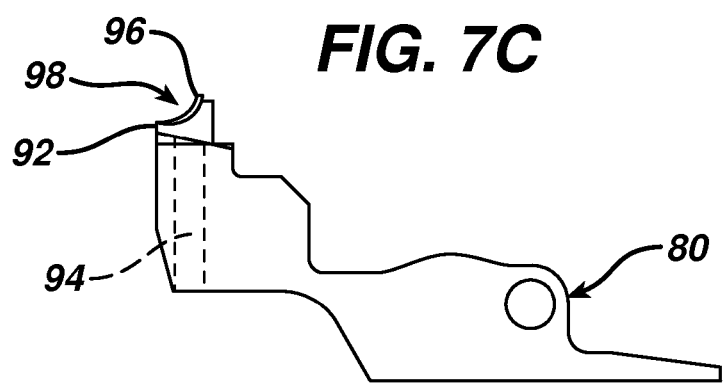
FIG. 7C shows a side elevation of the jaw.
Figure 7D:
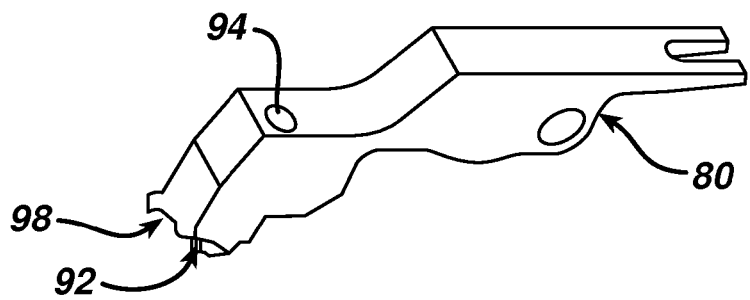
FIG. 7D shows a perspective view of the side and outer face of the jaw.

As previously stated, uncontrolled sealing of the excess end 22 of the overwrap 20 about the insertion end 32 of the tampon 30 can result in overwrap 20 sticking or being joined to the insertion end 32 of tampon 30. FIGS. 5 and 6 illustrate two stages commonly known in the prior art for sealing commercially available tampons, and described, e.g., in Simon et al., U.S. Pat. No. 3,856,143. In this process, a tampon is inserted into an overwrap tube that has one end 24' corresponding to the withdrawal end of the tampon sealed. The excess wrapper 22' at the insertion end is twisted causing the overwrap to conform to the surface of the tampon insertion end and forming a rope-like twisted structure 21'. Additional material extends beyond the twist 23' (See FIG. 5). The twisted 21' and excess 23' material is then folded over and conformed to the insertion end 32' of the tampon 30' (FIG. 6). Sufficient heat is applied to the now-closed end 22' of the overwrap 20' to conform it to the introduction end 32' of the tampon 30'. In the event that the overwrap material is not heat-sealable, e.g., cellophane, the heat may be necessary to set the excess material 23' in place. In the event that the overwrap material is heat-sealable, it may be necessary to provide sufficient heat to seal the excess material 23' to the rest of the overwrap material at the introduction end 32' of the tampon 30'. The result is an uneven surface having multiple melted layers on the insertion portion of the finished wrapped tampon. Too much heat would melt the layers and be conducted into the fibers of the tampon below the layers. In the tampons of the prior art, this was not an issue as the tampons did not have material such as meltable film covering the insertion end. With the new tampons shown in FIG. 2 and other tampons such as disclosed in Lochte et al. WO 2001/01909, a thermally sensitive material extends further to the introduction end 32 of the tampon 30. This thermally sensitive material is susceptible to thermal damage during the heat treatment of the overwrap end 22.

The present invention discloses a process, method and apparatus for sealing the overwrap about a tampon that does not result in the overwrap sticking to the tampon or tampon cover. The process also uses less material than the previous processes, which twist or otherwise form a rope-like structure before folding over and sealing to the outer surface.

In the present invention, multiple clamping jaws are spring mounted onto a fixed hub. The tampon is moved into position and the clamping jaws close about the insertion end of the tampon, pressing the overwrap toward the central longitudinal axis of the tampon (shown FIG. 9). Each jaw tip contains a heating element, which is used to preheat the jaw. The jaw momentarily contacts the overwrap, causing the overwrap to surround the insertion end of the tampon and be sealed together. The overwrap may extend beyond the insertion end if excess material is used. The jaws are then released, allowing the tampon to move to the folding station where the excess overwrap is folded and sealed back onto the overwrap covering the insertion end. In this invention the required time or temperature to accomplish the sealing and folding is less than the previous methods as there are fewer and more uniform layers or bulk for the heat to penetrate. For example, in one commercial example (O.b.® tampons, available from Personal Products Company, Skillman, N.J., USA) in which the overwrap was twisted into a rope and then folded over, the excess overwrap required was at least ⅝" of material. The temperature required to finish the insertion end of the overwrap was about 150 to 200° C. for about 0.2 seconds. In the present invention, the length of the excess material may be decreased by at least about 40% (to about ⅜"). The finishing temperature is decreased to about 1250 to 160° C. with substantially the same dwell time.

Figure 8A:
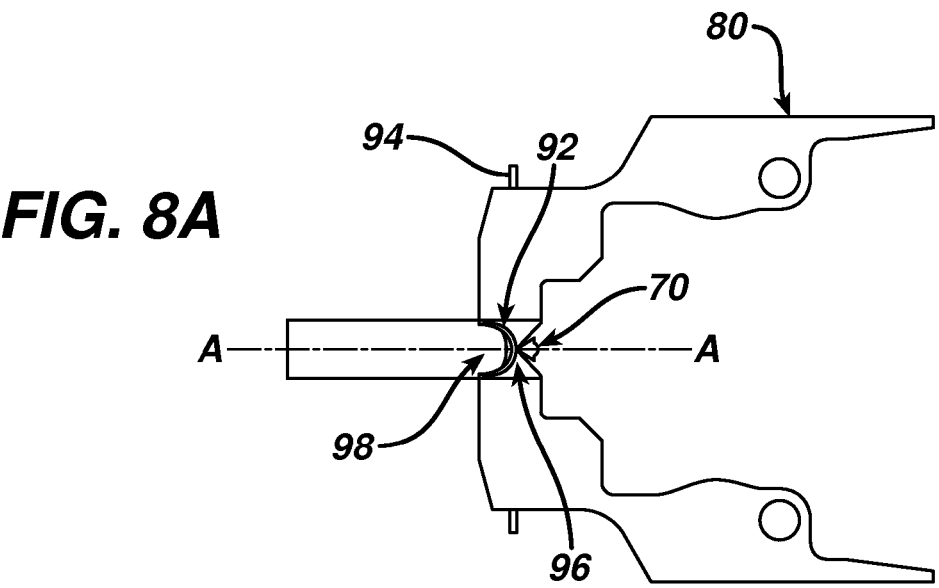
FIG. 8A shows a side elevation of two opposed jaws of the apparatus with a tampon disposed in the recess of the apparatus.
Figure 8B:
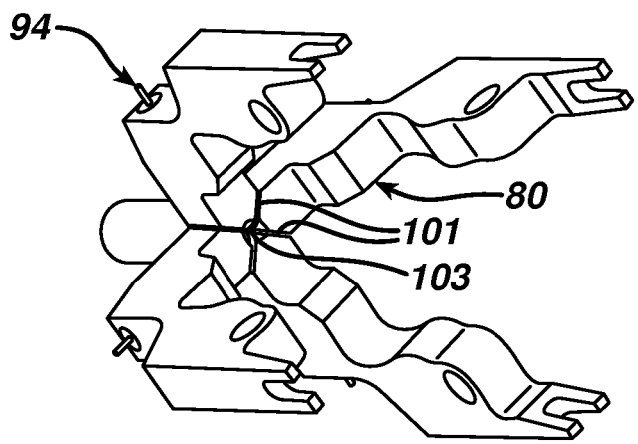
FIG. 8B shows a perspective view of the two jaws of FIG. 8B in the closed position.
Figure 8C:
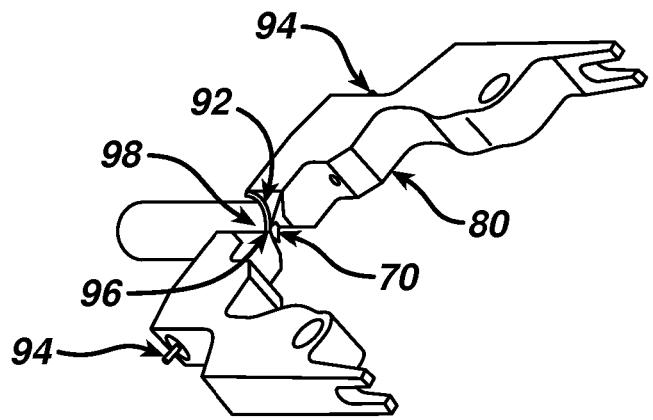
FIG. 8C shows a perspective view of four jaws in the closed position.

Turning to FIGS. 7 and 8, an example of a jaw of the present invention is shown. As shown, jaw 80 includes contacting end 90 and pivoting end 100. Contacting end 90 includes a sealing surface 92 and heating element (insertable through bore 94), which penetrates into the contacting end 90 such that the contacting surface 92 is capable of being heated to a predetermined temperature. Sealing surface 92 is the edge that extends from a concave recess or receiving area region 98 that is of complementary shape to the insertion end of the tampon and includes leading edge 96. The overwrap is sealed together by the heat and pressure of sealing surface 92 of a first jaw contacting the sealing surface 92 of a second jaw. Leading edge 96 urges the overwrap toward the central axis A-A of the tampon while sealing surface 92 and concave recess 98 form the base of the overwrap seal such that the tubular overwrap conforms to the surface of the insertion end of the tampon. During the process, the excess overwrap material that protrudes beyond the insertion end of the tampon is held in the concave recess 98.

In the present invention, there are at least three clamping jaws and may include more. In one embodiment, it has been found that four clamping jaws form an efficient apparatus that seal the excess overwrap, nicely conforming the overwrap about the insertion end of a tampon. The overwrap that protrudes beyond the tampon is sealed in four quadrants about the central longitudinal axis. As more jaws are used, less overwrap material may be required resulting in less waste.

Since sealing surface 92 of the jaw may be preheated before use, the contact time for sealing may be short. In one embodiment, the overwrap material is a polypropylene sheet with a temperature range of about 125° C. to 150° C., for about 0.15 to about 0.3 seconds, preferably about 0.23 seconds. Other materials may have different melting points, so the jaws may be maintained at a temperature appropriate to quickly seal the material used for the overwrap. As the material covering the insertion end of the tampon may have a similar melting point, it is important that the jaws not remain in contact with the overwrap for a long period of time in order to prevent the transfer of heat through the overwrap material.

Figure 10:
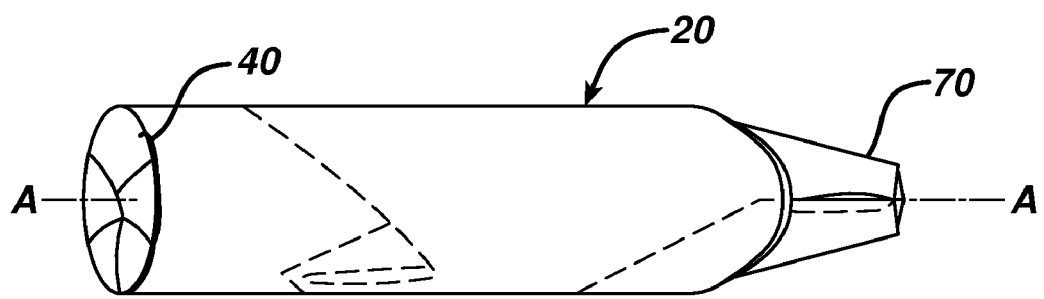
FIG. 10 shows a perspective view of tampon after sealing by the clamping jaws of the present invention.
Figure 11:
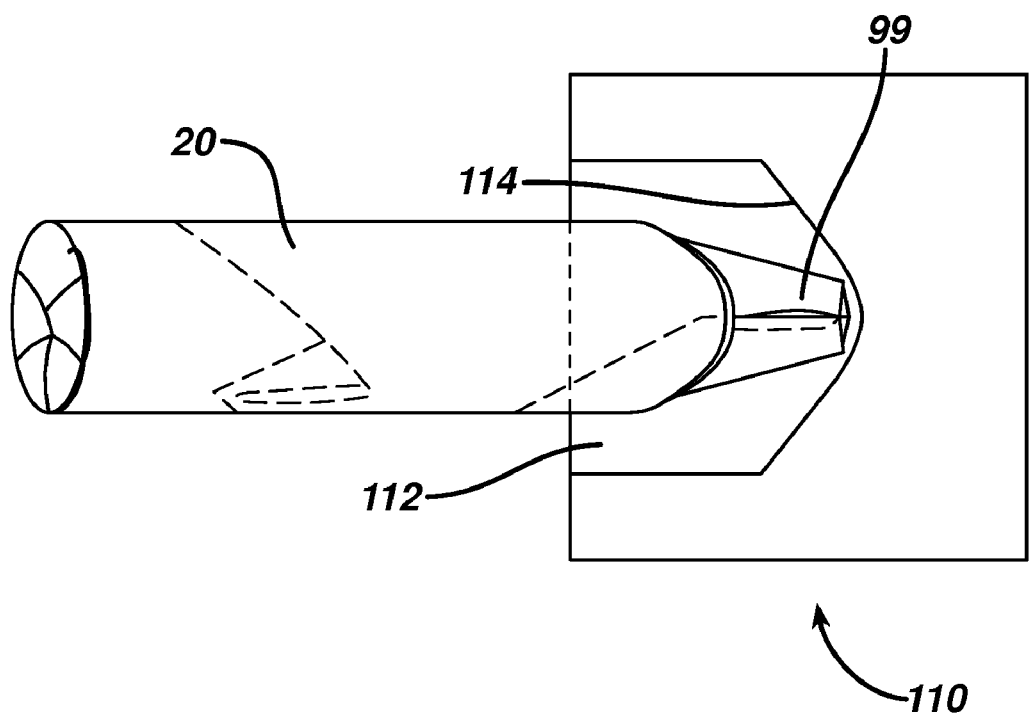
FIG. 11 shows a schematic view of a sealed tampon wrapper in a finishing station.

In one embodiment, the overwrap is sealed using four jaws. The sealing surface 92 and the concave recess area 98 of jaw 80 are uniformly aligned at 0° to the longitudinal axis A-A. This allows the overwrap to be sealed symmetrically into radial sections about the longitudinal axis of the tampon and has the excess material 70 extending along the axis. The sealed radial sections (fins 99 as shown in FIG. 10) are then folded to conform to the end surfaces of the overwrap end 22 in a separate finishing station 110 that has a substantially domed recess 112. Again, the inner sealing surface 114 of this finishing recess 112 may be provided with heating elements to allow the surface to expose the fins 99 to a temperature of about 130-160° C. In this embodiment with substantially longitudinal fins 99, the finishing may result in squashing of the fins 99 so the material lies close to the surface of the insertion end overwrap (See FIG. 11).

Figure 12:
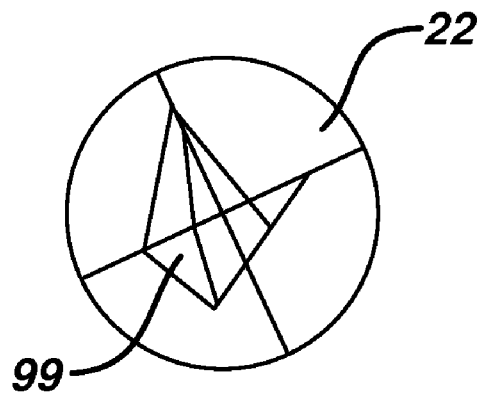
FIG. 12 shows a top plan view of one embodiment of the present invention.
Figure 13:
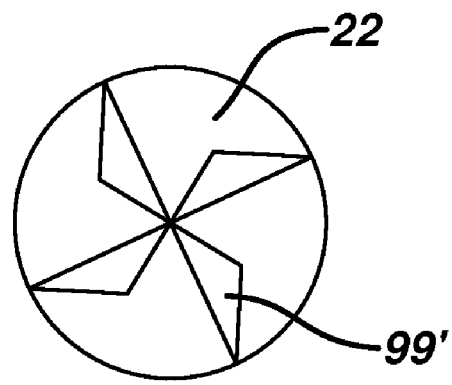
FIG. 13 shows a top plan view of an alternate embodiment of the present invention.

In another embodiment, contact surface 92 is positioned at an angle to the longitudinal axis A-A. For example, the angle may be offset sufficient to urge the fins 99 into a pinwheel configuration as shown in FIG. 12. Preferably, the offset is at least about 5°, and more preferably at least about 10°, e.g., about 12°. A preferred range is about 10° to about 30°, more preferably about 12° to about 24°.

The offset sealing surface 92' forms fins 99' that are at an angle to the longitudinal axis as shown in FIG. 9. As can be seen in FIG. 9E, the parting lines 101 between the sealing surfaces no longer form an "x" as is the case in the straight structure of FIG. 8. Instead the inner vertex 103 of the sealing surfaces is offset. This permits them to be folded over in a flatter manner. By using clamping jaws set in an offset angle to the longitudinal axis of the tampon, it is possible to use less heat for finishing the insertion end overwrap as the ultimate thickness of the overwrap is reduced and more uniformly distributed about the insertion end of the package device.

Tampon 30 has a compressed, elongated absorbent structure 36. The absorbent structure may include a fluid storage element having a longitudinal axis. The absorbent structure may also include ribs and grooves such as those described in EP 0 422 660. In one embodiment shown in FIG. 2, the absorbent structure is substantially surrounded by a primary cover 50, which is attached to the sliver prior to compression and a secondary cover 60, which overlays the primary cover 50. The secondary cover 60 may form at least one fluid transport element as disclosed in Chase et al., U.S. Ser. No. 10/847,952, published as US 2005-0256511 A1, the disclosure of which is herein incorporated by reference.

In one preferred embodiment, the absorbent structure 36 is an absorbent catamenial tampon 30. Absorbent tampons are usually substantially cylindrical masses of compressed absorbent material having a central axis and a radius that defines the outer circumferential surface of the tampon. Such tampons are disclosed in e.g., Haas, U.S. Pat. No. 1,926,900; Dostal, U.S. Pat. No. 3,811,445; Wolff, U.S. Pat. No. 3,422,496; Friese et al., U.S. Pat. No. 6,310,296; Leutwyler et al., U.S. Pat. No. 5,911,712, Truman, U.S. Pat. No. 3,983,875; Agyapong et al., U.S. Pat. No. 6,554,814; and Chase et al., US 2005-0256511 A1. Tampons also usually include a fluid-permeable cover (which may include or be replaced by another surface treatment) and a withdrawal string or other removal mechanism. The primary cover 50 is fluid-permeable.

The absorbent structure can be made of any composition known in the art, such as compressed fibrous webs, rolled goods, foam etc. The storage element can be made of any material known in the art such as cotton, rayon, polyester, superabsorbent material, etc.

Fibers may be selected from cellulosic fiber, including natural fibers (such as cotton, wood pulp, jute, and the like) and synthetic fibers (such as regenerated cellulose, cellulose nitrate, cellulose acetate, rayon, polyester, polyvinyl alcohol, polyolefin, polyamine, polyamide, polyacrylonitrile, and the like).

Absorbent materials useful in the formation of the absorbent body include fiber, foam, superabsorbent, hydrogels, and the like. Preferred absorbent material for the present invention includes foam and fiber. Absorbent foams may include hydrophilic foams, foams that are readily wetted by aqueous fluids as well as foams in which the cell walls that form the foam themselves absorb fluid.

A withdrawal mechanism, such as withdrawal string 40, is preferably joined to the tampon 30 for removal after use. The withdrawal mechanism is preferably joined to at least the tampon 30 and extends beyond at least its withdrawal end 34. Any of the withdrawal strings currently known in the art may be used as a suitable withdrawal mechanism, including without limitation, braided (or twisted) cord, yarn, etc. In addition, the withdrawal mechanism can take on other forms such as a ribbon, loop, tab, or the like (including combinations of currently used mechanisms and these other forms). For example, several ribbons may be twisted or braided to provide parallel plates structures.

In particular, materials useful for forming the secondary cover 60 (or fluid transport element) may have properties such as thermobondability to provide means to incorporate it into the intravaginal device. A representative, non-limiting list of useful materials includes polyolefins, such as polypropylene and polyethylene; polyolefin copolymers, such as ethylenevinyl acetate ("EVA"), ethylene-propylene, ethyleneacrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. The secondary cover 60 may also be micro-embossed or apertured. Examples of films having apertures include for example, three-dimensional apertured films, as disclosed in Thompson, U.S. Pat. No. 3,929,135, and Turi et al, U.S. Pat. No. 5,567,376, as well as two-dimensional reticulated film, such as that described in Kelly, U.S. Pat. No. 4,381,326. The material used for the secondary cover 60 may have a melting point of less than or equal to the melting point of the overwrap.

The compressed tampon 30 is packaged in an overwrap 20 comprising a polymeric film in contact with the secondary cover 60 and containing the tampon 30 under compression. The overwrap 20 is removable from the compressed tampon 30 during use.

The overwrap 20 may be chosen from a wide variety of commonly used wrapper materials such as polymeric films or metal foils or even treated papers. The overwrap 20 is rolled about the cylindrical tampon and the end 24 is sealed closed by means of heat sealing, by the use of adhesives or by simply twisting, folding or crimping closed. The transverse edge 28 is sealed closed. The wrapper is to be removed from the tampon by pulling up tab 29 located in the transverse edge 28 of the wrapper to tear the wrapper and free the tampon.

EXAMPLE

Example 1

Tampons were made according to US 2005-0256511 A1 and prepared for packaging according to the present invention. The length of excess overwrap material before sealing was measured to be ¼ inch. After sealing to form fins, the overwrap had an excess length of ⅛ inch. The excess was sealed and folded over at a temperature of about 135° C. for 0.23 seconds without damage to the secondary cover of the packaged tampon.

What is claimed is:

1. A process for overwrapping a catamenial device such as a tampon comprising the steps of:
 a) providing a substantially cylindrical overwrapper material having an open end, a closed end, a first length, and a diameter;
 b) inserting a catamenial tampon having a tapered insertion end, a longitudinal axis, and a length less than the first length into the cylindrical overwrapper material, the open end of the overwrapper material extending parallel to the longitudinal axis beyond the insertion end of the inserted catamenial tampon; and
 c) closing the open end of the overwrapper material by:
  i) applying at least three concave clamping jaws to the open end of the overwrapper material to urge the overwrapper material toward the longitudinal axis of the catamenial tampon, wherein the excess overwrapper material extends along the longitudinal axis; to conform portions of the overwrapper material to the insertion end of the catamenial tampon; and to seal overwrapper material between adjacent clamping jaws to form fins extending outwardly from the conformed portions along the longitudinal axis wherein said fins do not extend beyond said diameter of the overwrapper perpendicular to the longitudinal axis; and
  ii) pressing the fins to the conformed portions of the overwrapper material.

2. The process of claim 1, wherein each fin extends outwardly in a plane substantially parallel to the longitudinal axis.

3. The process of claim 1, wherein each fin extends outwardly in a plane offset at least about 5° from the longitudinal axis.

4. The process of claim 3, wherein each fin extends outwardly in a plane offset by about 10° to about 30° from the longitudinal axis.

5. The process of claim 1, wherein the step of closing the open end of the overwrapper material comprises applying four concave clamping jaws.

6. The process of claim 1, wherein the step of applying the clamping jaws to seal overwrapper material between adjacent clamping jaws further comprises heating the overwrapper material.

7. The process of claim 6, wherein the step of heating the overwrapper material comprises heating the overwrapper material to about 150 to 200° C. for about 0.2 seconds.

8. The process of claim 1, wherein the step of pressing the fins to the conformed portions of the overwrapper material further comprises heating the overwrapper material.

9. The process of claim 8, wherein the step of pressing the fins and heating the overwrapper material comprises heating the overwrapper material to about 125° to 160° C. for about 0.2 seconds.

10. Apparatus for closing an overwrapper material about a rounded end of a cylindrical tampon, the apparatus comprising:
 a) a clamping device comprising at least three clamping jaws, each jaw having a recess area and at least one sealing surface, each sealing surface having means to heat the surface operatively connected thereto, wherein the recess areas of adjacent clamping jaws are capable of closing about a rounded end of a generally cylindrical tampon having a diameter perpendicular to a longitudinal axis to conform overwrapper material about the rounded end and folding excess overwrapper material between a sealing surface on a first clamping jaw and an opposed sealing surface on an adjacent clamping jaw to permit the excess overwrapper material to extend along the longitudinal axis and to form fins extending outwardly from the longitudinal axis that do not extend beyond said diameter of the tampon perpendicular to the longitudinal axis; and
 b) a finishing former arranged and configured to conform the outwardly extending fins to the rounded end of the generally cylindrical tampon.

11. The apparatus of claim 10, wherein adjacent clamping jaws meet in a plane substantially parallel to the longitudinal axis.

12. The apparatus of claim 11, wherein adjacent clamping jaws meet in a plane including the longitudinal axis.

13. The apparatus of claim 10, wherein adjacent clamping jaws meet in a plane offset at least about 5° from the longitudinal axis.

14. The apparatus of claim 13, wherein adjacent clamping jaws meet in a plane offset by about 10° to about 30° from the longitudinal axis.

15. The apparatus of claim 10, wherein the clamping device comprises four clamping jaws.

16. The apparatus of claim 10, wherein the clamping jaws further comprise means to heat the jaws.

* * * * *